United States Patent
Fisker (10) Patent No.: US 10,433,938 B2
(45) Date of Patent: Oct. 8, 2019

(54) METHOD FOR DESIGNING ATTACHMENT ABUTMENTS FOR ATTACHING DENTURES TO THE MANDIBLE AND/OR MAXILLA

(71) Applicant: 3SHAPE A/S, Copenhagen K (DK)

(72) Inventor: Rune Fisker, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 190 days.

(21) Appl. No.: 15/035,857

(22) PCT Filed: Nov. 11, 2014

(86) PCT No.: PCT/EP2014/074274
§ 371 (c)(1),
(2) Date: May 11, 2016

(87) PCT Pub. No.: WO2015/071261
PCT Pub. Date: May 21, 2015

(65) Prior Publication Data
US 2016/0287360 A1    Oct. 6, 2016

(30) Foreign Application Priority Data

Nov. 12, 2013 (DK) .................................. 2013 70673

(51) Int. Cl.
*A61C 8/00* (2006.01)
*A61C 13/271* (2006.01)
*A61C 13/00* (2006.01)

(52) U.S. Cl.
CPC ............ *A61C 8/0056* (2013.01); *A61C 8/005* (2013.01); *A61C 8/0066* (2013.01);
(Continued)

(58) Field of Classification Search
CPC ............ A61C 13/0004; A61C 13/0027; A61C 8/0077; A61C 8/0074; A61C 8/0068;
(Continued)

(56) References Cited

U.S. PATENT DOCUMENTS 5,989,029 A    11/1999  Osorio et al.
6,030,219 A *   2/2000  Zuest ................... A61C 8/0048
                                                              433/172

(Continued)

FOREIGN PATENT DOCUMENTS

CN    102078224 A    6/2011
EP    2 025 303 A1   2/2009
(Continued)

OTHER PUBLICATIONS

International Search Report (PCT/ISA/210) dated May 19, 2015, by the European Patent Office as the International Searching Authority for International Application No. PCT/EP2014/074274.
(Continued)

*Primary Examiner* — Khamdan N. Alrobaie
(74) *Attorney, Agent, or Firm* — Buchanan Ingersoll & Rooney PC (57) ABSTRACT

Disclosed is a method for digitally designing at least two attachment abutments, each attachment abutment comprising an implant connection section adapted for connection to a respective implant along an implant axis, a transition section separating the implant connection section and an attachment section, wherein the attachment section is adapted for receiving a mating part.

15 Claims, 4 Drawing Sheets

(52) U.S. Cl.
CPC .......... *A61C 8/0068* (2013.01); *A61C 8/0074* (2013.01); *A61C 8/0077* (2013.01); *A61C 13/0027* (2013.01); *A61C 13/26* (2013.01); *A61C 8/0053* (2013.01)

(58) Field of Classification Search
CPC ..... A61C 8/0056; A61C 8/0066; A61C 8/005; A61C 13/26; A61C 8/0051
See application file for complete search history.

(56) References Cited

U.S. PATENT DOCUMENTS

| | | | |
|---|---|---|---|
| 6,994,547 B1* | 2/2006 | Sethi | A61C 8/005 433/172 |
| 2007/0092854 A1* | 4/2007 | Powell | A61C 13/0004 433/213 |
| 2008/0026338 A1* | 1/2008 | Cinader | A61C 1/084 433/29 |
| 2008/0050700 A1 | 2/2008 | Weber et al. | |
| 2008/0227058 A1* | 9/2008 | Karmon | A61C 8/005 433/174 |
| 2009/0047629 A1 | 2/2009 | Kim | |
| 2009/0111071 A1 | 4/2009 | Yau et al. | |
| 2010/0304334 A1 | 12/2010 | Layton | |
| 2011/0171599 A1* | 7/2011 | Seo | A61C 8/005 433/173 |
| 2012/0296613 A1 | 11/2012 | Kirchner et al. | |
| 2012/0315599 A1* | 12/2012 | Mullaly | A61C 8/0048 433/173 |
| 2013/0004919 A1 | 1/2013 | Kirchner et al. | |
| 2013/0209958 A1* | 8/2013 | Benz | A61C 8/005 433/173 |
| 2014/0162212 A1* | 6/2014 | Mullaly | A61C 8/0053 433/173 |
| 2014/0283738 A1 | 9/2014 | Gradert | |
| 2015/0025855 A1* | 1/2015 | Fisker | A61C 8/0077 703/1 |
| 2015/0073577 A1 | 3/2015 | Fisker et al. | |
| 2015/0202024 A1* | 7/2015 | Fisker | A61C 8/008 433/213 |

FOREIGN PATENT DOCUMENTS

| | | |
|---|---|---|
| EP | 2 123 235 A1 | 11/2009 |
| WO | WO 2007/062658 A2 | 6/2007 |
| WO | WO 2013/083682 A1 | 6/2013 |

OTHER PUBLICATIONS

Written Opinion (PCT/ISA/237) dated May 19, 2015, by the European Patent Office as the International Searching Authority for International Application No. PCT/EP2014/074274.

Search Report dated Jun. 20, 2014, issued by the Danish Patent Office in the European Application No. PA 2013 70673.

* cited by examiner

METHOD FOR DESIGNING ATTACHMENT ABUTMENTS FOR ATTACHING DENTURES TO THE MANDIBLE AND/OR MAXILLA

FIELD OF THE INVENTION

This invention generally relates to a method for designing attachment abutments for attaching a denture to the maxilla and/or mandible of a patient. More particularly, the invention relates to a method for designing attachment abutments which are customised for improved fit and esthetics.

BACKGROUND OF THE INVENTION

Standard stock attachment abutments used for attaching dentures to the maxilla and/or mandible are known.

The attachment abutment is formed with a connection section adapted for connection to an implant and an attachment section adapted for connection to a denture.

The stock abutments typically have a connection section that fits with generally used implants. The attachment sections differs from manufacturer to manufacturer. Some provide ball attachments and other have ring-shaped attachment sections that fit with mating caps provided in the denture. Well known manufactures of standard stock attachment abutments are for example Zest Anchors who manufacture the Locator® attachment and Implant Direct who manufacture the GPS system which is compatible with the Locator® system. Ball attachments are for example manufactured by Nobel Biocare and MIS implants.

The attachment section typically allows some sort of pivot with respect to the mating part. This allows for connection to the denture even when the attachment abutments are at different angles. However, when such angulations between the attachment section and mating part occurs the retention force is reduced. In particular it can be difficult to determine the actual retention force.

There are provided different systems wherein the retention force can be increased, however, these systems have a lower angle at which the connection can be established and maintained.

In the following the angle range within which the attachment section can move with respect to the mating part in the denture is referred to as the pivot angle or pivoting tolerance. I.e. a pivot angle of 20° allows for a pivoting movement of the mating part relative to the attachment section of between 0 and 20 degrees. The pivot angle or pivoting tolerance is a term commonly used in the art.

However, there is a need for customized attachment abutments, and in particular, a method for designing attachment abutment for improved fit and esthetics of the denture to be attached thereon.

SUMMARY

Disclosed is a method for digitally designing at least two attachment abutments, each attachment abutment comprising an implant connection section adapted for connection to a respective implant along an implant axis, a transition section separating the implant connection section from an attachment section, wherein the attachment section is adapted for receiving a mating part, the method comprises the steps of, obtaining a digital 3D representation of at least a part of a jaw comprising information on the location and orientation of at least two implants extending along respective implant axes within the jaw represented by the digital 3D representation, selecting the shape of the respective connection section from a set of pre-determined digital connection shapes for each attachment abutment, aligning the implant connection sections of the attachment abutments to coextend along the implant axis of the respective implants, selecting the shape of the respective attachment section from a set of pre-determined digital attachment shapes for each attachment abutment, generating the transition section extending between the respective connection section and the respective attachment section of each abutment attachment.

This enables a configuration of the attachment abutments with improved attachment to a denture wherein the mating part is retained.

As can be understood the connection section and attachment section needs to interface with set shapes, e.g. the connection section needs to interface with the implant and the attachment section needs to be able to attach to the mating part. Accordingly, these parts are predetermined and cannot be modified during design without risking that the fit is compromised and/or risking severe pain for the patient.

In the following the term "jaw" refers to the maxilla and the mandible of a patient or a part thereof. For example, the 3D representation may represent either the maxilla or the mandible, a part of both or the complete maxilla and mandible whereby the full jaw is represented.

The following disclosure discusses a method for digitally designing an attachment abutment and other parts, which may be provided during such a design process, e.g. the mating part and a denture. It should thus be understood that any reference to a design or modeling step refers to the digitally design method and not to a manually design method unless specifically stated so. Moreover, when referring to a product, e.g. the attachment abutment, it can be understood that the reference can be to the digital model thereof or to the manufactured physical model.

In one embodiment the method further comprises the step of digitally arranging each attachment section according to at least one common design criteria.

When using a digital design environment as disclosed herein it is particularly advantageous to be able to design the attachment abutments according to a common design criteria as the digital design environment facilitates very accurate methods of designing each attachment abutment according to said design criteria.

In one embodiment the at least one common design criteria comprises rules for arranging each attachment section to extend parallel to each other. This ensures that a denture will easily attach to the attachment abutment along a specific insertion direction of the denture. In particular where attachment abutments and corresponding mating parts are used which have a very low degree of pivoting tolerance it is important to maintain the same insertion direction for all attachment abutments.

Alternatively or additionally the at least one common design criteria may further comprise rules for arranging each attachment section to be level with each other. A level arrangement reduces the risk that the attachment of the denture becomes unstable or 'wobbly'. By level it should be understood that the attachment sections are designed to the same horizontal plane. The horizontal plane may for example be parallel to the occlusal plane of the patient, or by parallel to a plane defined by the inter-pupillary line, i.e. the line extending between the two pupils of the patient.

In one specific embodiment thereof one attachment section is arranged with a minimum vertical height. This provides the attachment sections in a configuration where the attachment abutments are level at the minimum height possible.

The term "minimum/minimal vertical height" is a commonly used term within attachment abutments. It is a value that gives the minimal height necessary for the attachment abutment to extend above the gingiva in order to maintain attachment to the denture and the integrated mating part, which is attached to the attachment abutment. Within a digital environment where the mandible and/or the maxilla has been obtained by a surface scan, this distance could be measured from the surface of the 3D representation to the top of the attachment section of the attachment abutment.

Accordingly, in one embodiment the at least one common design criteria advantageously comprises rules for arranging each attachment section with a minimum vertical height. This provides a setup which has the least exposure of attachment abutment surfaces above the gingiva and accordingly provides a high degree of flexibility when designing the denture and have a reduced risk of shine through of the attachment abutments through the artificial gingiva.

Preferably the set of pre-determined digital connection and/or attachment shapes are selected from a digital library comprising a number of CAD files each describing a pre-determined shape.

The connection shape is determined based on the implant type placed in the jaw. Typically this information is either given separately from the dentist, or is provided in the digital 3D representation. Based on this, the correct connection shape can be selected automatically by the computer running the described method as only one shape will be correct in order to ensure proper fit and connection of the attachment abutment with the implant.

When designing in a digital environment it becomes possible to provide highly customized attachment abutments. This can for example be done in one embodiment where at least one of the attachment abutments is designed so that the attachment section extend along an axis different from the implant axis In yet another embodiment the method further comprises matching a corresponding mating part for the corresponding selected attachment section for each attachment abutment.

As described the attachment abutments are used for securely attaching dentures to the jaw of the patient, accordingly, in one embodiment the method may advantageously further comprise digitally designing a denture wherein the mating parts are retained and are aligned to the respective attachment sections of the attachment abutments.

An initial digital denture is preferably designed before designing the attachment abutments. In this way the esthetics and function of the denture is considered before placing the attachment abutments.

In order for the dentist to place the manufactured attachment abutment correctly in the patient a transfer tray can be designed and manufactured. However, since the attachment section typically is symmetrical there is a risk that the attachment abutment will rotate in the transfer tray. This creates a risk that the attachment abutment is placed incorrect. Accordingly, in one embodiment the method further comprises digitally designing a locking element on the surface of the attachment section, thereby creating an asymmetric surface on the attachment section. The locking element can for example be a protrusion or a recess.

Accordingly, the asymmetric surface prevents the attachment abutment from rotating in the transfer tray.

In one aspect, there is disclosed a method for digitally designing a transfer tray for use with at least one attachment abutment comprising an implant connection section adapted for connection to a respective implant along an implant axis, a transition section separating the implant connection section from an attachment section, wherein the attachment section is adapted for receiving a mating part, wherein the method comprises,
  obtaining a digital design of least one attachment abutment comprising an asymmetric surface on the attachment section, and
  digitally designing a transfer tray based on the at least one digital design of an attachment abutment.

As mentioned above, by providing an asymmetric design on the attachment section rotation of the attachment abutment is prevented in the transfer tray.

In one embodiment the step of digitally designing a transfer tray based on the at least one digital design of an attachment abutment comprises,
  designing a digital splint model defining a geometrical volume,
  arranging at least a part of the attachment section of the digital design of the at least one attachment abutment within the geometrical volume,
  subtracting the volume of the digital design of the at least one attachment section arranged within the geometrical volume from said geometrical volume.

The subtraction can for example be performed by a Boolean subtraction, which is an operation well known in the art.

The method for digitally designing at least two attachment abutments and for digitally designing a transfer tray are typically executed on a computer. E.g. a data storage medium, such as a hard drive, stores computer code, which when executed by a data processor performs the one or more of the steps according to the method.

For example the step of obtaining the 3D representation may involve loading a data file from an external source. However, it may also involve the actual step of scanning.

The steps for digitally selecting the shapes of the connection and attachment section may involve the user selecting an appropriate shape from a list of a number of library shape. However, based on information included in e.g. the 3D representation the computer may suggest an appropriate shape or even automatically determine the correct shape.

The step for digitally aligning may be executed automatically by the computer. But may also allow the user to modify the alignment if needed.

The step of digitally generating the transition section may involve a suggested shape design by the computer. However, the user may modify the shape of the transition section by manipulating control points thereon.

The user may interact with the digital method through a digital design environment. This digital design environment may comprise a monitor whereon the digital 3D representation and the digital designs of the attachment abutments may be visualized for the user and the user may use a mouse and/or a keyboard or similar input devices to interact with the digital design environment. The mouse can for example be used to activate different tools provided in the digital design environment.

In another aspect there is disclosed a digital design environment for designing at least two attachment abutment, each attachment abutment comprising an implant connection section adapted for connection to a respective implant along an implant axis, a transition section separating the implant connection section from an attachment section, wherein the attachment section is adapted for receiving a mating part, the digital design environment comprises,
- a digital work space adapted for visualizing a digital 3D representation of at least a part of a jaw comprising information on the location and orientation of at least two implants extending along respective implant axes within the jaw represented by the digital 3D representation,
- a digital connection section selection tool for selecting the shape of the respective connection section from a set of pre-determined digital connection shapes,
- a digital alignment tool for aligning the implant connection sections of the attachment abutments to coextend along the implant axis of the respective implants when activated,
- a digital attachment section selection tool for selecting the shape of the respective attachment section from a set of pre-determined digital attachment shapes, and
- a digital arrangement tool for arranging each attachment section according to at least one common design criteria when activated.

Such a digital design environment provides tools for aiding the dental technician in performing the method as described herein. In particular by customizing specific tools to perform specific actions when activated the method is facilitated.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
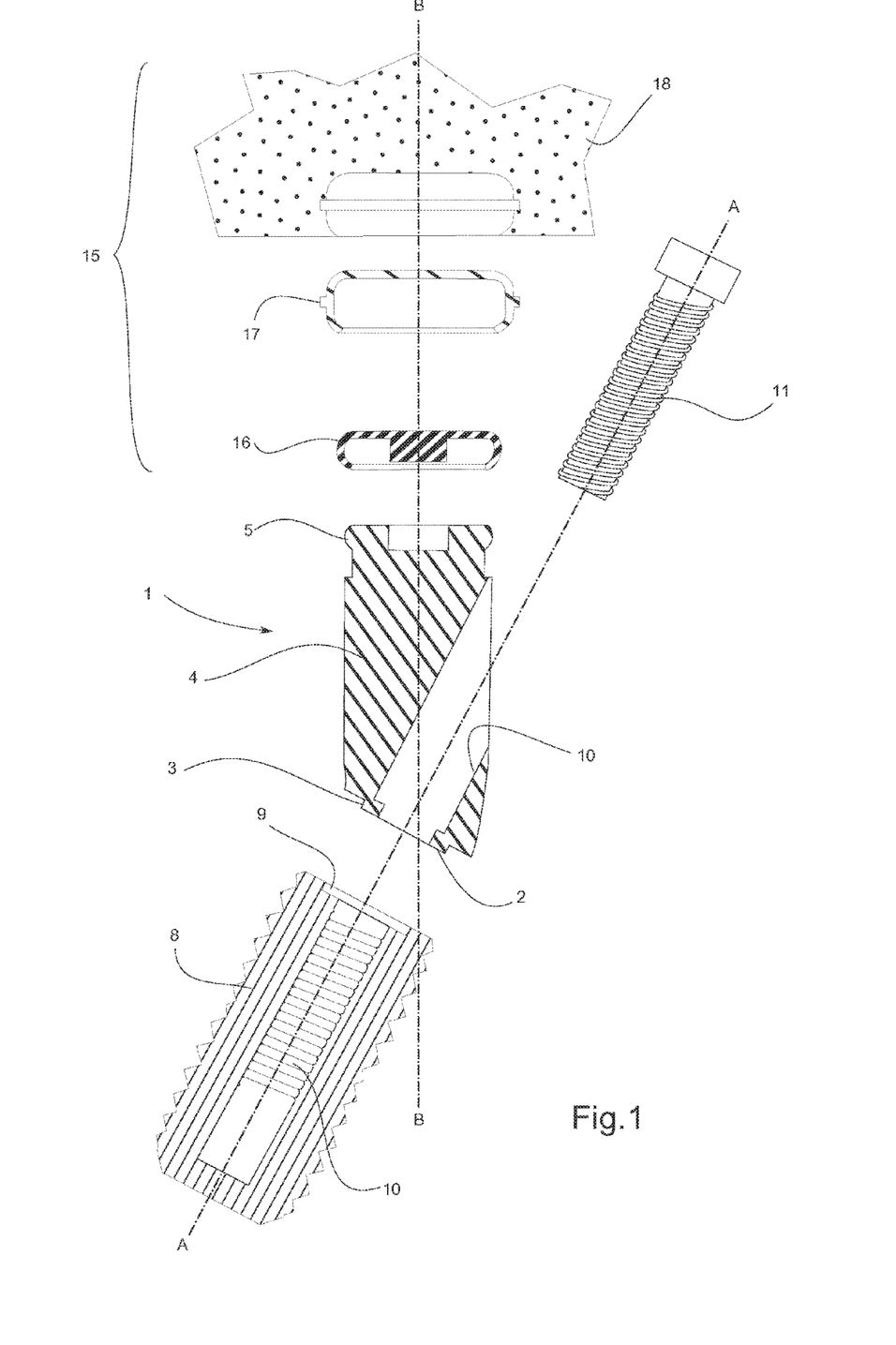
FIG. 1 shows an embodiment of an attachment abutment designed by using the method as disclosed herein.

FIG. 1 shows an embodiment of an attachment abutment 1 designed by using the method as disclosed herein.

The attachment abutment 1 comprises a connection section 2 for connecting with an implant 8 along an implant axis A-A. In the current embodiment the connection section comprises a connection interface in the shape of an annular protrusion 3 extending coaxially along the implant axis. A corresponding annular recess 9 is provided in the implant 8.

Preferably, although not shown, the annular protrusion and recess have an asymmetric shape. This ensures that the attachment abutment and the implant are connected in only one possible position relative to each other and prevents rotation of the attachment abutment in the implant.

A screw bore 10 extending through the attachment abutment and into the implant 8 are provided in order to connect the implant and the attachment abutment by a screw 11. Such means are generally known from e.g. other abutment and implant assemblies known from prior art.

A transition section 4 separates the connection section 2 from an attachment section 5.

The attachment section 5 is configured to receive a mating part 16 which is part of a mating assembly 15. In the current embodiment the mating assembly comprises the mating part 16 which fits into a cap 17 which is adapted to be integrated into the artificial gingiva 18 of a denture. Numerous such attachment sections and mating assemblies have been disclosed, for example the Locator system manufactured by Zest Anchors.

The transition section 4 is designed so that the attachment axis B-B, which is the axis along which the attachment section and mating assembly extends along in a preferred direction providing for optimal connection of a denture 18.

Figure 2A:
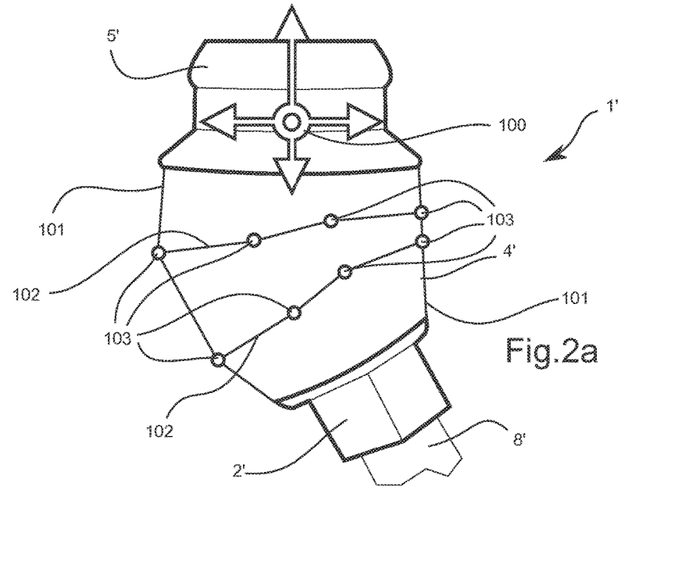
FIGS. 2a and 2b shows an embodiment a design interface for an attachment embodiment and an interface for designing a number of attachment abutments using a common design criteria.
Figure 2B:
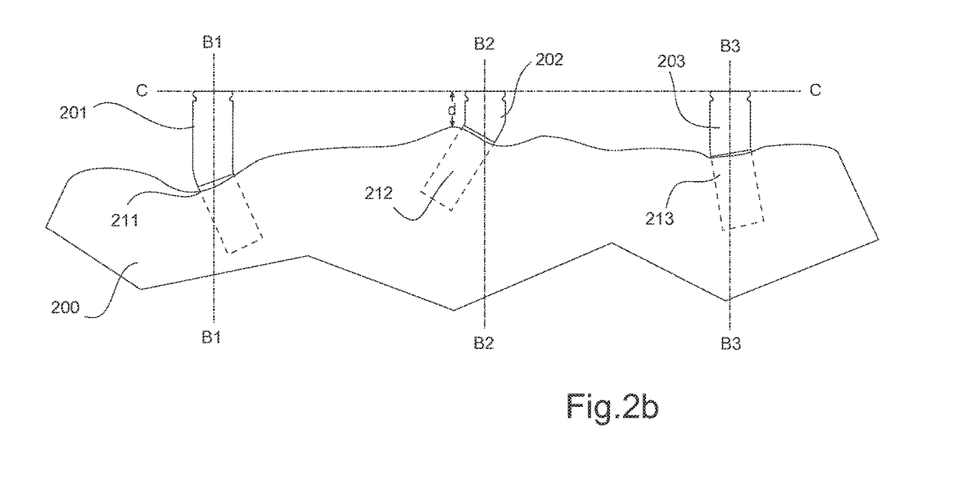

With reference to FIGS. 2a and 2b it is described how the attachment abutment can be designed in a digital design environment and how several attachment abutments can be designed relative to each other in an advantageous manner as disclosed herein.

In FIG. 2a a digital model of a customized attachment abutment 1' is shown. The digital attachment abutment is visualized with several design tools 100, 101, 102, 103 overlaid.

The digital connection section 2' is chosen based on the type of implant placed in the jaw. In the digital design environment the digital connection section is aligned with a digital representation of the implant 8'. If the user attempts to change this alignment and place the connection section 2' differently a warning will alert the user that any change may result in that the final attachment abutment will not fit the implant, or may even cause injury to the patient.

With the digital connection section 2' automatically aligned the user will now chose a digital attachment section 5' from a library of digital attachment sections.

After choosing the digital attachment section 5' it is placed in the digital design environment and the user can move it around by manipulating the main control point 100. The user can move the digital attachment section 5' to fit one of the design rules as will be described below in respect to FIG. 2b or it can be placed in respect to a digital denture that is also placed and visually represented in the digital design environment. The digital denture may be a scan of a patients denture, a scan of a wax rim or a digital designed model of a denture that will be sent to production along with the attachment abutments after the digital design phase is done.

As the user moves the digital attachment section 5' around a digital transition section 4' will be dynamically generated and connects the digital attachment section and the digital connection section. Curvature profiles 101 and 102 can be manipulated in order to change the shape of the digital transition section 4' by moving the curvature control point 103.

When the digital design of the digital attachment abutment 1' is complete it is ready to be sent to manufacturing.

The digital design environment may furthermore comprise some design rules or design guides as will be described in the following with respect to FIG. 2b. A digital gingiva 200 is provided in the digital design environment. The digital gingiva is obtained by scanning the gingiva itself intra-orally or by scanning a physical representation thereof, e.g. a dental impression of the mandible or maxilla or a gypsum model and thus the digital gingiva represents the physical gingiva of a patient.

Accordingly, it is desired to provide a denture (not shown) for the patient which is attached to the jaw of the patient by a first, second and third attachment abutment, represented by the digital attachment abutments 201, 202, 203, via mating assemblies (not shown) provided in the denture.

The first, second and third attachment abutments are connected to respective first, second and third implants, represented by the digital implants 211, 212, 213 for example as disclosed with respect to FIG. 1. The location and orientation of the implants can be transferred into the digital environment as known in the art. Such transfer is for example disclosed in WO2007/062658.

The respective connection sections of the attachment abutment are formed to match and fit the respective implants. Accordingly, these can be chosen from a digital library of pre-designed digital representations of connection sections in the digital design environment. Any amendments to the designs should be avoided as this may compromise the connection to the implant.

Similarly are the respective attachment section of the attachment abutments formed to match and fit respective mating assemblies (not shown) provided in a denture (not shown). Thus, it is also advantageous that these are chosen from a library of pre-designed parts and not further altered in order to prevent that attachment to the mating assembling is compromised.

Accordingly, it is the intermediate part, i.e. the transition section, which is modeled and altered in order to change the shape and angle of the attachment abutment.

As shown in FIG. 2, the transition section have been modeled so that the attachment abutment are placed securely in the respective implant, while each attachment section extends along respective attachment axis B1-B1, B2-B2 and B3-B3, wherein these axis extend parallel with each other.

By providing attachment abutment which thereby extend parallel to each other ideal condition is generated for optimal attachment to a denture (not shown). The denture may be designed manually, or it may be designed digitally in a further work flow in the digital environment.

In addition to designing the attachment abutments to extend in parallel they can also be designed with a minimum vertical height 'd', which is the minimum distance from the surface of the gum to the top of the attachment section of the attachment abutment possible while still obtaining correct attachment to the denture.

Each attachment abutment can be designed so that each has a minimum vertical height or they can be designed against a horizontal reference line C-C wherein one attachment abutment have the minimum vertical height 'd'.

Figure 3A:
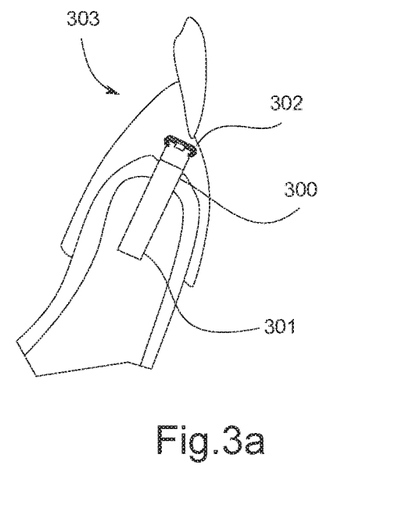
FIGS. 3a and 3b shows one of the advantages of using the method as disclosed herein.

Another advantage of designing attachment abutments as described herein is that they enable improved esthetical options. For example as illustrated in FIG. 3a, a standard abutment attachment 300 which extends along the implant axis is connected to an implant 301. The edge of the attachment abutment is thereby placed very close to the labial surface of the artificial gingiva 302 of the denture 303. This result in that an area of the artificial gingiva has a darker hue since the attachment abutment shines through the material used to manufacture the gingiva.

Figure 3B:
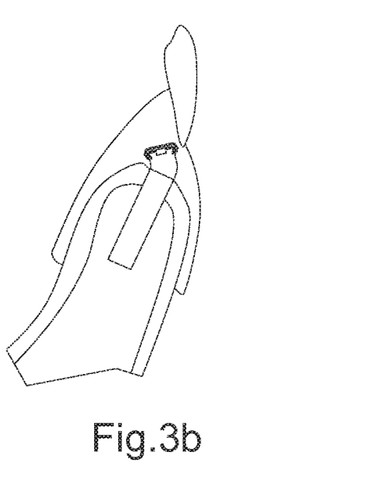

However, by designing the attachment abutment so that the attachment section extends along an axis different from the implant axis it is possible in some cases to prevent the shine through of the attachment abutment as it can be placed further away from the labial surface of the denture.

When designing an attachment abutment it is important to consider the placement of the screw bore for the implant screw as it is important that it does not interfere with the attachment section. If the design goes through the sides of the attachment section the attachment with the mating part may be compromised and the denture may not attach properly and fall out during wear.

As can be seen in FIG. 1 the screw bore 10 stays clear of the attachment section. This can be obtained when the transition section is long or the angle between the implant axis A-A and the attachment axis B-B is large.

However, at smaller angles or with shorter transition section other design may be necessary.

Figure 4A:
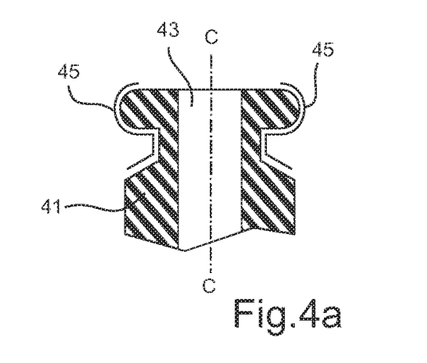
FIGS. 4a, 4b and 5 shows further embodiments of an attachment abutment designed using the method described herein.
Figure 4B:
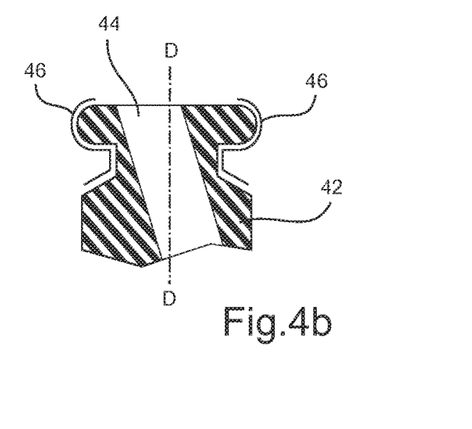

FIGS. 4a and 4b shows a design embodiment where the attachment section 41 and 42 are designed through which screw bores 43 and 44 for the implant screw (not shown) are provided that extend through the respective attachment sections. However, the screw bores does not extend through the load surfaces 45 and 46 and thus there is no risk of compromising the function of the attachment abutment. The load surfaces are the surfaces of the attachment abutment that engages with the mating part when a force is applied to the denture during wear, e.g. when chewing.

As can be seen the screw bore can be designed to extend at a slight angle to the attachment axis D-D in FIG. 4b which allows for a small angulation of the attachment abutment.

However, at slightly larger angles or if ball attachments are used it is not possible to allow any design modifications to the attachment section.

Figures 5, 7:
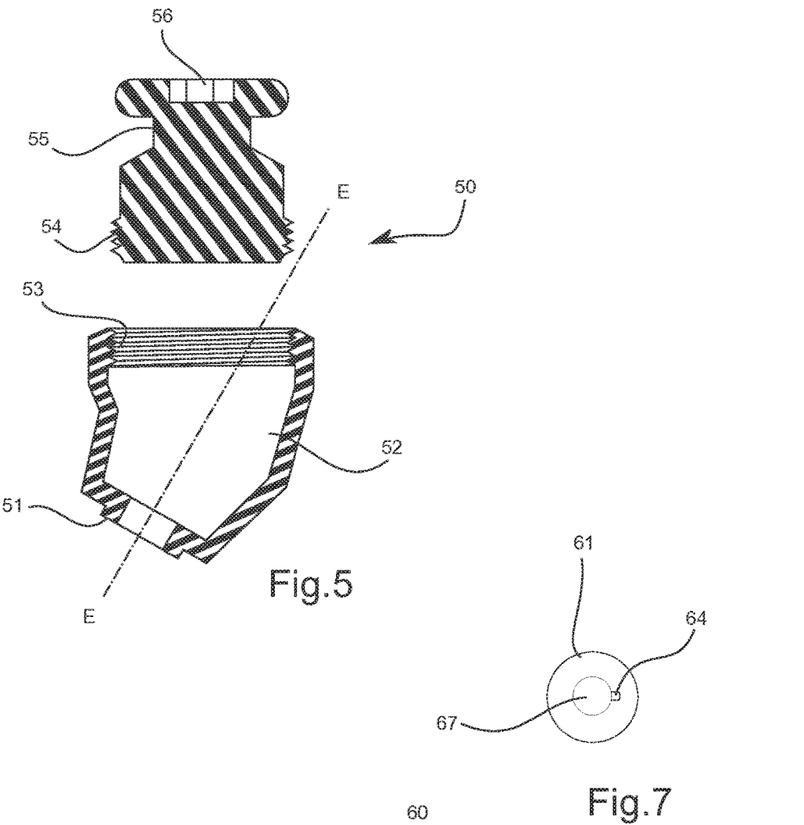
FIGS. 6 and 7 shows a transfer tray for placing attachment abutment in the jaw and an attachment abutment suitable for use in a transfer tray.

In this case the digital attachment abutment 50 is split into at least two pieces before manufacturing as shown in FIG. 5.

The connection section 51 and transition section 52 are provided in one piece wherein it is possible to insert the implant screw along the implant axis E-ED. An internal thread 53 is provided on the transition section that engages with an external thread 54 of the attachment section 55. When placed in the implant the connection section and attachment section is first fixed to the implant and afterwards the attachment section is screwed in by an appropriate tool that fits into the slot 56, e.g. an Unbrako® key.

If the attachment section is a ball attachment design (not shown) a hexagon design could be provided on the outer surface below the ball which will allow for a torque wrench to engage and screw the ball attachment into place.

When placing the final manufactured attachment abutments it is important that they are placed correctly in the implant. In other words, the dentist have to be careful to not rotate them into a wrong position.

Figure 6:
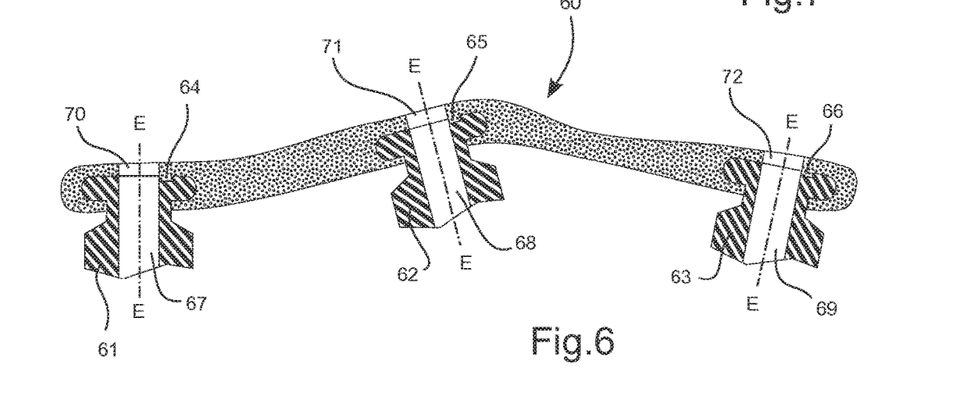

In order to avoid this a transfer tray 60 can be produced and used as shown in FIG. 6. A transfer tray is a splint that arranges attachment abutments in their correct position in the jaw. In the described embodiment the transfer tray receives three attachment abutments 61, 62 and 63.

However, since typical attachment abutments have symmetrical attachment section there is a high risk of undesired rotation in the transfer tray and thus, there is a risk that the attachment abutment is rotated and placed incorrectly in the implants.

In order to prevent that the attachment abutment rotates in the transfer tray an asymmetry is generated in the attachment section with which the transfer tray can engage. This results in that the attachment abutment is prevented from rotating whereby attachment abutment can be placed correctly in the implant.

In the embodiment illustrated in FIGS. 6 and 7 this asymmetry is created by a locking slot 64, 65 and 66 that extends radially from the screw bores 67, 68 and 69 along the surface of the respective attachment section of the attachment abutments.

The asymmetry created by the locking slot prevents the attachment abutments from rotating in the transfer tray and the attachment abutments can be placed correctly in the implants. The attachment abutments are fixed by inserting an implant screw through the implant screw bore 67, 68 and 69 and co-axially extending screw bores 70, 71 and 72 formed in the transfer tray.

Of course, such asymmetry can be provided in many ways in order to prevent rotational movement around the attachment axis E-E of the attachment abutments.

During use the transfer tray is typically used to place one attachment abutment at the time, in particular when each abutment have different insertion directions into the respective implants. Alternatively, separate transfer trays could be made for each attachment abutment, or for attachment abutments having same or similar insertion directions.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method for digitally designing at least two attachment abutments, each attachment abutment comprising an implant connection section adapted for connection to a respective implant along an implant axis, a customized transition section separating the implant connection section from an attachment section, wherein the attachment section is adapted for engaging with a denture along a denture attachment axis, wherein the denture attachment axes for the at least two attachment abutments are parallel, the method comprises the steps of, obtaining a digital 3D representation of at least a part of a jaw comprising information on the location and orientation of at least two implants extending along respective implant axes within the jaw represented by the digital 3D representation, wherein the respective implant axes are not parallel with each other and are not parallel with the denture attachment axes, obtaining information about portions of the at least two implants that are adapted to be attached to the respective connection sections, digitally selecting a shape of a connection section from a set of pre-determined digital connection shapes for each attachment abutment based on the obtained information, digitally selecting a shape of a respective attachment section from a set of pre-determined digital attachment shapes for each attachment abutment, for each attachment abutment, digitally aligning the respective implant connection section of the attachment abutment to coextend along the implant axis of the respective implant, for each attachment abutment, moving the respective attachment section according to at least one common design criteria, and in response to moving the respective attachment section, dynamically customizing the transition section extending between the respective connection section and the respective attachment section of each abutment attachment so that the attachment section is aligned with the denture attachment axis, wherein the method further comprises the step of digitally arranging each attachment section according to the at least one common design criteria and the at least one common design criteria comprises rules for arranging each attachment section to extend parallel to each other.

2. The method according to claim 1, wherein one attachment section is arranged with a minimum vertical height.

3. The method according to claim 1, wherein the set of pre-determined digital connection and/or attachment shapes are selected from a digital library comprising a number of CAD files each describing a pre-determined shape.

4. The method according to claim 1, wherein the method further comprises digitally designing at least one of the attachment abutments so that the attachment section extend along an axis different from the implant axis.

5. The method according to claim 1, wherein the method further comprises matching a corresponding mating part for the corresponding selected attachment section for each attachment abutment.

6. The method according to claim 1, wherein the method further comprises digitally designing a denture wherein the mating parts are retained and are aligned to the respective attachment sections of the attachment abutments.

7. The method according to claim 1, wherein the method further comprises digitally designing a locking element on the surface of the attachment section, thereby creating an asymmetric surface on the attachment section.

8. The method according to claim 7, wherein the locking element is a protrusion or a recess.

9. The method according to claim 1, wherein the method further comprises digitally generating the customized transition section extending between the respective connection section and the respective attachment section of each abutment attachment by manipulating control points on the transition section.

10. The method according to claim 1, wherein each digital connection section is aligned with a digital representation of a respective one of the implants, and emitting a warning when the alignment between a respective connection section and respective implant is incorrect.

11. The method according to claim 1, further comprising digitally designing a denture for attaching to the at least two attachment abutments based on the digital design of the at least two attachment abutments.

12. The method according to claim 1, further comprising manufacturing the at least two attachment abutments.

13. A method for digitally designing at least two attachment abutments, each attachment abutment comprising an implant connection section adapted for connection to a respective implant along an implant axis, a customized transition section separating the implant connection section from an attachment section, wherein the attachment section is adapted for engaging with a denture along a denture attachment axis, wherein the denture attachment axes for the at least two attachment abutments are parallel, the method comprises the steps of,
obtaining a digital 3D representation of at least a part of a jaw comprising information on the location and orientation of at least two implants extending along respective implant axes within the jaw represented by the digital 3D representation, wherein the respective implant axes are not parallel with each other and are not parallel with the denture attachment axes,
obtaining information about portions of the at least two implants that are adapted to be attached to the respective connection sections,
digitally selecting a shape of a connection section from a set of pre-determined digital connection shapes for each attachment abutment based on the obtained information,
digitally selecting a shape of a respective attachment section from a set of pre-determined digital attachment shapes for each attachment abutment,
for each attachment abutment, digitally aligning the respective implant connection section of the attachment abutment to coextend along the implant axis of the respective implant,
for each attachment abutment, moving the respective attachment section according to at least one common design criteria, and
in response to moving the respective attachment section, dynamically customizing the transition section extending between the respective connection section and the respective attachment section of each abutment attachment so that the attachment section is aligned with the denture attachment axis,
wherein the method further comprises the step of digitally arranging each attachment section according to at least one common design criteria and the at least one common design criteria comprises rules for arranging each attachment section to be level with each other.

14. A method for digitally designing at least two attachment abutments, each attachment abutment comprising an implant connection section adapted for connection to a respective implant along an implant axis, a customized transition section separating the implant connection section from an attachment section, wherein the attachment section is adapted for engaging with a denture along a denture attachment axis, wherein the denture attachment axes for the at least two attachment abutments are parallel, the method comprises the steps of,
obtaining a digital 3D representation of at least a part of a jaw comprising information on the location and orientation of at least two implants extending along respective implant axes within the jaw represented by the digital 3D representation, wherein the respective implant axes are not parallel with each other and are not parallel with the denture attachment axes,
obtaining information about portions of the at least two implants that are adapted to be attached to the respective connection sections,
digitally selecting a shape of a connection section from a set of pre-determined digital connection shapes for each attachment abutment based on the obtained information,
digitally selecting a shape of a respective attachment section from a set of pre-determined digital attachment shapes for each attachment abutment,
for each attachment abutment, digitally aligning the respective implant connection section of the attachment abutment to coextend along the implant axis of the respective implant,
for each attachment abutment, moving the respective attachment section according to at least one common design criteria, and
in response to moving the respective attachment section, dynamically customizing the transition section extending between the respective connection section and the respective attachment section of each abutment attachment so that the attachment section is aligned with the denture attachment axis,
wherein the method further comprises the step of digitally arranging each attachment section according to at least one common design criteria and the at least one common design criteria comprises rules for arranging each attachment section with a minimum vertical height.

15. A digital design environment for designing at least two attachment abutment, each attachment abutment comprising an implant connection section adapted for connection to a respective implant along an implant axis, a customized transition section separating the implant connection section from an attachment section, wherein the attachment section is adapted engaging with a denture along a denture attachment axis, wherein the denture attachment axes for the at least two attachment abutments are parallel, the digital design environment comprises,
a digital work space adapted for visualizing a digital 3D representation of at least a part of a jaw comprising information on the location and orientation of at least two implants extending along respective implant axes within the jaw represented by the digital 3D representation, wherein the respective implant axes are not parallel with each other and are not parallel with the denture attachment axes,
a digital connection section selection tool for selecting the shape of the connection section from a set of pre-determined digital connection shapes,
a digital alignment tool for aligning the implant connection sections of the attachment abutments to coextend along the implant axis of the respective implants when activated,
a digital attachment section selection tool for selecting the shape of the respective attachment section from a set of pre-determined digital attachment shapes,
a digital arrangement tool for arranging each attachment section according to at least one common design criteria when activated and the at least one common design criteria comprises rules for arranging each attachment section to extend parallel to each other, and
in response to arranging the respective attachment section, the transition section is dynamically customized to extend between the respective connection section and the respective attachment section of each abutment attachment so that the attachment section is aligned with the denture attachment axis.

\* \* \* \* \*